United States Patent [19]

Viglietti

[11] Patent Number: 4,604,057
[45] Date of Patent: Aug. 5, 1986

[54] CAST ORTHODONTIC APPLIANCE

[75] Inventor: John E. Viglietti, Sheboygan, Wis.

[73] Assignee: American Orthodontics Corporation, Sheboygan, Wis.

[21] Appl. No.: 751,903

[22] Filed: Jul. 3, 1985

[51] Int. Cl.⁴ ............................................. A61C 7/00
[52] U.S. Cl. ...................................................... 433/9
[58] Field of Search ................................. 433/8, 9, 16

[56] References Cited

U.S. PATENT DOCUMENTS

| | | | |
|---|---|---|---|
| 3,765,091 | 10/1973 | Northcott | 433/9 |
| 3,975,824 | 8/1976 | Lee | 433/9 |
| 4,165,561 | 8/1979 | Miller et al. | |
| 4,219,617 | 8/1980 | Wallshein | |
| 4,243,386 | 1/1981 | Kawaguchi | |
| 4,322,206 | 3/1982 | Reynolds | |
| 4,430,061 | 2/1984 | Webb et al. | 433/9 |

Primary Examiner—Robert Peshock
Attorney, Agent, or Firm—Lloyd L. Zickert

[57] ABSTRACT

A cast orthodontic appliance for bonding to a tooth having an appliance portion with an archwire slot and a pad or base portion with a curved tooth-conforming bonding surface. The bonding surface is formed with a plurality of horizontal or vertical grooves or slots opening lingually. The grooves on each side of center diverge.

7 Claims, 8 Drawing Figures

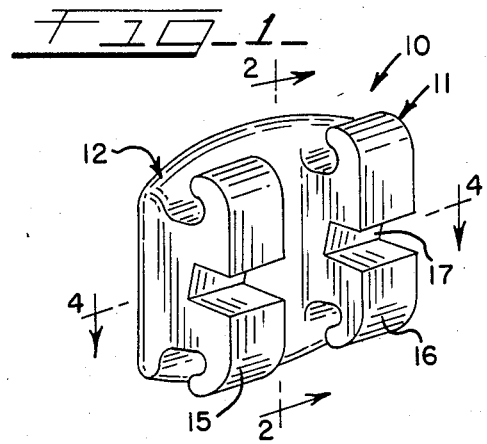
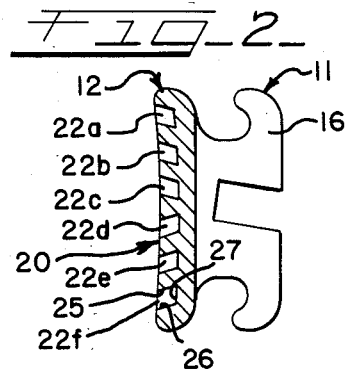
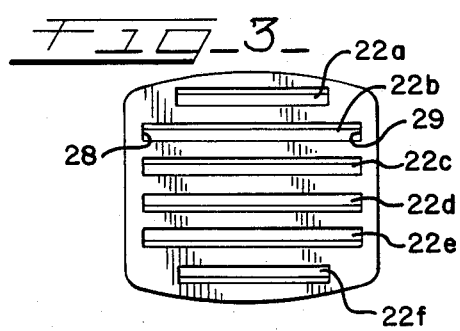
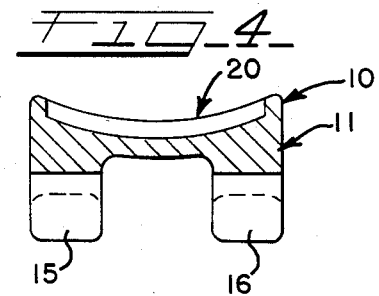
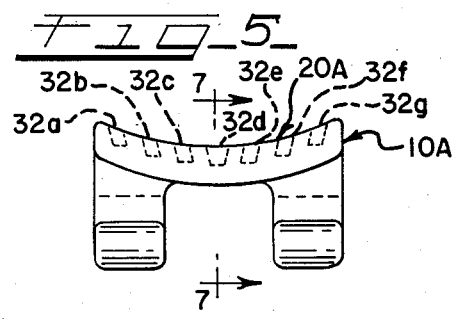
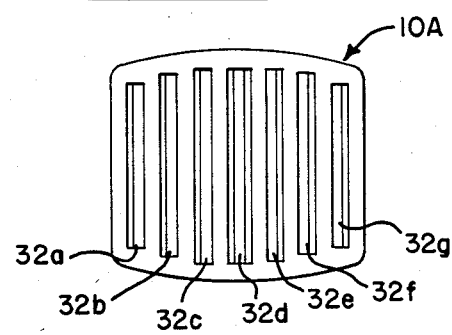
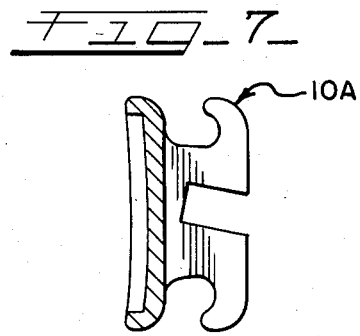
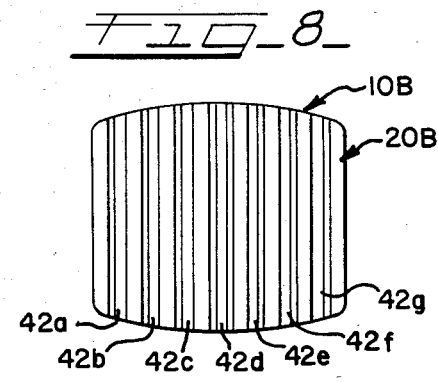

4,604,057

CAST ORTHODONTIC APPLIANCE

DESCRIPTION

This invention relates in general to orthodontic appliances, and particularly to orthodontic appliances that are directly bonded to teeth by use of a suitable bonding material, and still more particularly to a cast orthodontic appliance having an integrally formed pad or base with a unique curved tooth-conforming bonding surface.

BACKGROUND OF THE INVENTION

The practice of direct bonding orthodontic appliances such as brackets, tubes and the like to teeth has been long known. There are a number of bonding systems or adhesives on the market for use in direct bonding applications.

It has also been well known to attach appliances to bonding pads by welding or soldering procedures wherein the bonding pads have bonding surfaces of various types to produce the desired bond between the appliances and the teeth. The most well known and widely used bonding pad includes a mesh surface of the type illustrated in U.S. Pat. Nos. 4,068,379 and 4,165,561. It has also been known to provide a bonding surface that is dimpled as in U.S. Pat. No. 4,243,386. Other forms of surface structures have also been known.

Cast appliances having integrally formed bonding pads have also been known. Such integrally formed pads have bonding surfaces formed with holes, cavities and slots such as shown in U.S. Pat. Nos. 4,165,561 (FIGS. 17 and 20); 3,765,091 (FIGS. 1 and 5); and 4,322,206. It has also been known to provide a slotted bonding surface in a cast bracket where the slots on opposite sides of a midline converge toward the midline to define a V-lock configuration. With the advent of a trend toward having more cast brackets, either of metal by investment casting procedures or of plastic by plastic molding procedures, there has been a need to improve the bonding strength of a bracket to a tooth. Other types of metal molding procedures may also be used. While improvements have been made relative to the bonding materials or adhesives, attention has been directed toward improving the bonding strength through the construction of the bonding surface of the appliance.

SUMMARY OF THE INVENTION

The present invention is directed to an improved cast orthodontic appliance having a wire-handling portion and a pad portion cast as an integral unit which provides materially improved bonding strength with a unique bonding surface that can be economically manufactured with present-day manufacturing techniques. The cast appliance of the present invention may take the form of a bracket, a buccal tube, or other wire-handling appliances. It may also take the form of a lingual button or the like for attachment of an elastic. The present invention satisfies a need produced by the continuing demand for cast appliances where the base or pad portion is integrally formed with the appliance portion. The term "cast" as used herein is intended to cover an appliance cast or molded of metal or plastic.

It will be appreciated that the bonding surface of the pad portion according to the invention is uniquely formed to be suitable for direct bonding procedures used to directly bond appliances to teeth by appropriate bonding materials or adhesives such as those sold by American Orthodontics Corporation of Sheboygan, Wis.

The cast orthodontic appliance of the invention includes a pad portion having a tooth-conforming bonding surface which would be curved both occlusogingivally and/or mesiodistally for the particular tooth upon which the appliance is designed to be mounted and provided with either a series of parallel vertical or horizontal grooves or slots. The grooves opposite the vertical or horizontal midline would be slanted outwardly or diverging so as to provide the maximum area of tooth surface area exposed to the adhesive between the bonding surface and the tooth. This arrangement also facilitates the casting or molding procedures where dies are used for forming the grooves. Further, the slanting configuration of the grooves permits the use of the dies where a curved bonding surface is formed. Where the slots are slanted inwardly or converging, it is necessary to first make the bonding surface flat and thereafter resort to a secondary operation to curve the surface which is more expensive and which also could lead to damaging of the grooves.

It is an object of the present invention to provide a new and improved cast orthodontic appliance having an improved bonding surface on a pad portion integrally formed with the appliance wherein the bonding surface materially improves the bonding strength between the appliance and the tooth and also facilitates the manufacture of the appliance to reduce manufacturing costs.

Another object of the present invention is in the provision of a new and improved cast orthodontic appliance having a bonding pad portion integrally formed and a bonding surface with horizontal or vertical grooves that are angled to provide the maximum bonding strength and also to facilitate the manufacturing process.

A still further object of the present invention is in the provision of a cast orthodontic appliance having an integrally formed bonding pad with a bonding surface formed with a plurality of parallel grooves where the grooves on the opposite sides of a midline on the bracket slant outwardly or diverge.

Other objects, features and advantages of the invention will be apparent from the following detailed disclosure, taken in conjunction with the accompanying sheet of drawings, wherein like reference numerals refer to like parts, in which:

BRIEF DESCRIPTION OF THE DRAWINGS

FIG. 1 is a perspective view of a cast orthodontic appliance according to the invention;

FIG. 2 is a vertical sectional view of the appliance taken generally along line 2—2 of FIG. 1;

FIG. 3 is a rear view of the appliance of FIG. 1;

FIG. 4 is a horizontal sectional view taken generally along line 4—4 of FIG. 1;

FIG. 5 is a top plan view of a modification of the invention where the grooves in the bonding surface extend vertically;

FIG. 6 is a rear elevational view of the appliance of FIG. 5;

FIG. 7 is a vertical sectional view taken generally along line 7—7 of FIG. 5; and FIG. 8 is a rear elevational view of a further modified appliance where the grooves on the bonding surface extend through the opposite edges of the surface.

DESCRIPTION OF THE INVENTION

Referring now to the drawings and particularly to the embodiment of FIGS. 1 to 4, a cast orthodontic appliance 10 includes an appliance portion 11 and a bonding pad or base portion 12. The appliance 10 is in the form of a bracket although it should be appreciated that it might be in the form of a buccal tube, a lingual button or any other type of appliance that is adapted to be bonded to a tooth and utilized to orthodontically treat a patient. More particularly, the appliance portion 11 is in the form of a twin tie bracket including spaced tie or ligating wings 15 and 16 with a suitably positioned archwire slot 17.

The tie wings extend from the bonding pad or base portion 12 which includes a bonding surface 20 that is uniquely formed to coact with a bonding material for bonding to a tooth surface. Thus, the bonding pad or base 12 is integrally formed with the appliance portion 11. As above already noted, the appliance may be suitably investment cast or molded of metal or plastic or otherwise suitably formed such that the pad and bracket portions are integral.

The unique bonding surface of the invention in the embodiment of FIGS. 1 to 4 is defined by a plurality of parallel arranged grooves or slots 22a, 22b, 22c, 22d, 22e and 22f. The slots extend between the mesial and distal edges of the pad, terminating short of the edges. Thus, the slots do not extend through the edges of the bonding surface. Each of the slots includes parallel opposed side walls 25 and 26, a bottom wall 27 and parallel opposed end walls 28 and 29. It should be appreciated the end walls 28 and 29 may be slanted outwardly. The grooves on opposite sides of the horizontal midline diverge lingually at a suitable angle, thereby defining pockets for bonding material that are axially inclined from a horizontal plane extending through the appliance. The configuration of the slots facilitates the casting or molding of the appliance. Additionally, they coact with the bonding material to increase the area of contact and enhance the strength of the bond between the appliance and the tooth. Further, the slanting of the grooves defines a locking action with the bonding adhesive. Lastly, diverging the slots rather than converging them as in the prior art spreads the bonding over a wider area of the tooth, thereby increasing the strength of the bond.

As seen particularly in FIGS. 2 and 4, the bonding surface 20 is curved vertically and horizontally for the purpose of conforming to and mating with a tooth surface. It should be further appreciated that these curvatures will be such as to match the tooth on which the bracket is to be mounted while twin tie wings are shown. If the appliance portion is to be in the form of a bracket or wire handling device, it may consist of a single tie wing or multiple tie wings.

The embodiment of FIGS. 5, 6 and 7, generally designated by the numeral 10A, differs from the embodiment of FIGS. 1 to 4 in the arrangement of the grooves on the bonding surface 20A particularly because the grooves extend vertically of the appliance. The grooves are designated 32a, 32b, 32c, 32d, 32e, 32f and 32g. Again, the grooves on opposite sides of the vertical midline diverge lingually. For example, grooves 32a, 32b and 32c are axially inclined outwardly in one direction, while grooves 32e, 32f and 32g are axially inclined outwardly in the other direction. In this embodiment a center groove 32d is provided which has one side wall paralleling the axes of grooves 32a, 32b and 32c, and another side wall paralleling the axes of grooves 32e, 32f and 32g, as particularly seen in FIG. 5. The grooves in this embodiment likewise coact with the bonding material to bond the appliance to a tooth. It may be also understood and noted that the bonding surface is curved both horizontally and vertically to conform to a tooth surface as in the embodiment of FIGS. 1 to 4.

Referring now to FIG. 8 and the embodiment 10B, it differs from the embodiment 10A of FIGS. 5 to 7 only in that the grooves or slots on the bonding surface 20B extend through the upper and lower edges of the bonding surface. The grooves are designated as 42a, 42b, 42c, 42d, 42e, 42f and 42g. Again, the grooves 42a, 42b and 42c are slanted outwardly in one direction, while the grooves 42e, 42f and 42g are slanted outwardly in the other direction. Groove 42d is provided with opposite side walls that slant parallel to the respective axes of the grooves on the opposite sides of the bracket midline. It may also be appreciated that the horizontally arranged grooves may extend through the mesial and distal edges of the bonding surface with respect to the embodiment of FIGS. 1 to 4 even though such an arrangement is not illustrated.

In view of the foregoing, the cast orthodontic appliance of the present invention is seen to be provided with a unique bonding surface integrally formed that facilitates the manufacture of the appliance and also provides a strong bonding system between the appliance and the tooth.

It will be understood that modifications and variations may be effected without departing from the scope of the novel concepts of the present invention, but it is understood that this application is to be limited only by the scope of the appended claims.

I claim:

1. In a cast orthodontic appliance adapted to be bonded to a tooth with a bonding material including a pad portion having a bonding surface and an appliance portion extending from the pad portion, said bonding surface being curved to conform to a tooth surface receiving a bonding material to bond the appliance to a tooth, the improvement being in the bonding surface which includes a plurality of lingually opening parallel grooves, said grooves having substantially parallel opposed side walls, the axes of the grooves as defined by said side walls on opposite sides of the midline of the appliance diverging outwardly from each other, whereby a greater tooth surface bonding area is provided to interconnect the bracket and tooth through the bonding material.

2. The appliance of claim 1, wherein the grooves extend horizontally.

3. The appliance of claim 1, wherein the grooves extend vertically.

4. The appliance of claim 1, wherein the grooves terminate short of the edges of the bonding surface.

5. The appliance of claim 1, wherein the groovves extend through the edges of the bonding surface.

6. The appliance of claim 1, wherein the appliance portion is in the form of a wire receiving member.

7. The appliance of claim 1, wherein the appliance portion is in the form of a bracket.

* * * * *